United States Patent [19]
Koch

[11] Patent Number: 5,431,661
[45] Date of Patent: Jul. 11, 1995

[54] ADAPTER AND MATING TROCAR ELEMENT FOR USE IN TROCAR ASSEMBLY

[75] Inventor: Durmus Koch, Demarest, N.J.
[73] Assignee: Bipore, Inc., Northvale, N.J.
[21] Appl. No.: 146,240
[22] Filed: Nov. 2, 1993
[51] Int. Cl.⁶ .............................................. A61M 25/00
[52] U.S. Cl. ...................................... 606/108; 604/272
[58] Field of Search .............. 606/108, 167, 185, 222, 606/224; 604/48, 51, 264, 272–274, 280, 283, 284

[56] References Cited

U.S. PATENT DOCUMENTS

| | | | |
|---|---|---|---|
| 3,861,393 | 1/1975 | Durand | 604/274 |
| 4,360,024 | 11/1982 | Wallace | 604/283 |
| 4,431,426 | 2/1984 | Groshong et al. | 604/272 |
| 4,432,764 | 2/1984 | Lopez . | |
| 4,490,136 | 12/1984 | Ekbladh et al. | 604/272 |
| 4,569,675 | 2/1986 | Prosl et al. | 604/280 |
| 4,684,369 | 8/1987 | Wildmeersch | 604/272 |
| 4,792,328 | 12/1988 | Beck et al. | 604/272 |
| 4,832,687 | 5/1989 | Smith, III | 604/51 |
| 4,883,474 | 11/1989 | Sheridan et al. | 606/108 |
| 4,976,684 | 12/1990 | Broadmax, Jr. | 604/272 |
| 5,074,846 | 12/1991 | Clegg et al. . | |
| 5,092,848 | 3/1992 | DeCiutits | 604/272 |
| 5,092,849 | 3/1992 | Sampson . | |
| 5,147,336 | 9/1992 | Wendell et al. . | |
| 5,193,545 | 3/1993 | Marsoner et al. | 604/48 |
| 5,205,821 | 4/1993 | Kruger et al. . | |
| 5,215,538 | 6/1993 | Larkin . | |
| 5,234,438 | 8/1993 | Semrad | 606/108 |
| 5,306,240 | 4/1994 | Berry | 606/108 |

FOREIGN PATENT DOCUMENTS 322195 11/1971 U.S.S.R. .............................. 604/272

Primary Examiner—Stephen C. Pellegrino
Assistant Examiner—Nancy Mulcare
Attorney, Agent, or Firm—Klauber & Jackson

[57] ABSTRACT

An adapter 10 and a mating trocar element 20 for use in a trocar assembly 30. The adapter 10 is cylindrical in shape with a continuous bore 12 running therethrough. A first end 14 of the adapter 10 has a reduction in diameter and a second end 16 of the adapter 10 is internally threaded 18 along the bore 12. The first end 14 is sized so as to allow frictional engagement with the end of a mating flexible tube 32. The reduction in diameter of the first end 14 preferably corresponds to the wall thickness of the mating flexible tube 32, so as to maintain a continuous outer surface between the adapter 10 and the mating tube of constant outer diameter. The second end 16 is internally threaded 18 along the bore 12 so as to allow fastenable engagement with a threaded end 24 of the mating trocar element 20. The mating trocar element 20 has the shape of a rod with a first end 22 being formed with or machined to a sharp point and a second end 24 having a reduction in diameter which is threaded 26 so as to mate with the threaded bore 18 of the adapter 10. The reduction in diameter of the second end 24 preferably corresponds to the wall thickness of the threaded bore portion 18 of the adapter 10, so as to maintain a continuous outer surface between the trocar element 20 and the adapter 10 of constant outer diameter.

26 Claims, 4 Drawing Sheets

ADAPTER AND MATING TROCAR ELEMENT FOR USE IN TROCAR ASSEMBLY

BACKGROUND OF THE INVENTION

1. Field of the Invention

The present invention relates to trocar assemblies and, more particularly, to an adapter for use in trocar assemblies and a trocar element that mates therewith.

2. Description of the Prior Art

Following certain surgical procedures, such as hip and/or knee surgery, blood and other bodily fluids often accumulate in body cavities at the site of the surgery and are retained in body tissues, or adjacent thereto, until they are drained. Such fluids are typically drained with drainage tubes that are implanted during the surgical procedure for use in a post-operative setting. Conventionally, such drainage tubes are comprised of a piece of flexible poly vinyl chloride (PVC) tubing having a series of regularly spaced pores or perforations formed therein. In practice, the tubing is threaded through the site of the surgery by an attached needle-like device called a trocar and is thereafter configured in such a fashion as to permit fluids, such as blood, to either be drained or positively drawn therefrom.

A problem that occurs in the use of such a conventional trocar assembly is that the trocar, which is typically fabricated of a cylindrical piece of metal having a sharp point at one end and barbs at the other end, and the tubing are force/friction fit together at the barbed end of the trocar in such a manner that prevents their direct separation. Consequently, the tubing and the trocar must be separated by cutting the tubing thereby leaving a portion of the tubing still attached to the trocar. This manner of separation prompts physicians to discard the trocar when the surgical procedure is completed. This is both wasteful and uneconomical as the materials from which a trocar is conventionally manufactured are valuable and the cost of replacing a trocar, when considered on a volume basis, can be very high. A more economical approach would allow a trocar to be reused following sterilization.

Although not specifically directed toward the use of trocars, there are several patents that are directed toward attaching the end of a flexible tube or a catheter with other medical related devices. For example, in U.S. Pat. Nos. 4,432,764 by Lopez, 5,092,849 by Sampson, 5,205,821 by Kruger et al., 5,147,336 by Wendell et al., 5,215,538 by Larkin, and 5,074,846 by Clegg et al., devices are disclosed for adapting to or mating with the ends of tubes and/or catheters. A brief description of these devices will now be given.

In U.S. Pat. No. 4,432,764, an antiseptic end cap for a catheter is disclosed having an adapter member with a first outwardly threaded end and a second reduced diameter end for frictional engagement with a flexible tube. The adapter member is used in combination with a cap member that mates with the threaded end of the adapter member.

In U.S. Pat. No. 5,092,849, an implantable device is disclosed having an adapter element with a first outwardly threaded end and a second frictional fit end for frictional engagement with a flexible tube. The adapter element is used in combination with a septum element that mates with the threaded end of the adapter element.

In U.S. Pat. No. 5,205,821, a terminal reservoir capping device is disclosed having a tube connector element with a first outwardly threaded end and a second frictional fit end for frictional engagement with a flexible tube. The tube connector element is used in combination with a capping member that mates with the threaded end of the tube connector element.

In U.S. Pat. No. 5,147,336, an adapter kit for a catheter introducer is disclosed having a female luer adapter with a first outwardly threaded end and a second frictional fit end for frictional engagement with a flexible tube. The female luer adapter is used in combination with a male luer cap that mates with the threaded end of the female luer adapter.

In U.S. Pat. No. 5,215,538, an in-line valve for medical tubing is disclosed having a multi-component unit displaying a threaded engagement means at one end.

Lastly, in U.S. Pat. No. 5,074,846, a stoma creator is disclosed having first and second frictional fit ends for frictional engagement with flexible tubes of varying diameters.

Although all of the above-mentioned prior art devices allow for adapting or mating with the ends of tubes and/or catheters, none are directed toward the use of trocars nor are they concerned with the reusability of trocar assemblies. Furthermore, none of the above-described devices disclose the specific construction of the adapter and mating trocar element of the present invention, which will now be described.

SUMMARY OF THE INVENTION

The present invention contemplates an adapter for use in trocar assemblies and a trocar element that mates therewith. The adapter is fabricated of a rigid material, such as plastic or metal, and has a cylindrical shape with a continuous bore running therethrough. The first end of the adapter has a reduction in outer diameter and the second end of the adapter is internally threaded along the bore. The outer diameter of the first end is sized so as to allow frictional engagement with the end of a mating flexible tube. To firmly secure the first end of the adapter to the end of the mating flexible tube, various types of adhesives may be used. The reduction in outer diameter of the first end of the adapter preferably corresponds to the wall thickness of the mating tube, so as to maintain a continuous outer surface of constant outer diameter between the adapter and the mating tube when they are engaged. The second end of the adapter is internally threaded along the bore so as to allow engagement with a threaded end of the trocar element.

The trocar element is similar to a traditional trocar element in that it is typically fabricated of metal and has the shape of a rod with a first end being machined to a sharp point. However, a second end of the trocar element has a reduction in diameter and is threaded so as to mate with the threaded bore of the adapter. The reduction in diameter of the second end of the trocar element preferably corresponds to the wall thickness of the threaded bore portion of the adapter, so as to maintain a continuous outer surface of constant outer diameter between the trocar element and the adapter when they are mated. Such a constant outer diameter continuous surface between the trocar element and the adapter and, as previously described, between the adapter and the mating tube, provides a constant diameter trocar assembly. Such a constant diameter trocar assembly is critical since the trocar element, and hence the adapter and the mating tube, must pass through human flesh and body tissues with as little surface resistance as possible.

The benefit of the present invention adapter and the mating trocar element is that they may be easily separated by disengaging their threaded ends, thereby promoting reuse of the trocar upon sterilization. Furthermore, the rigidness of the adapter insures that the adapter will not collapse under the frictional engagement pressure of the mating tube, or that both the adapter and the mating tube will not collapse under substantial external pressure, thereby resulting in restricted fluid flow through the adapter and the mating tube. The rigidness of the adapter also insures that the adapter can easily mate with other devices, such as flexible tube junctions.

From the above descriptive summary it is apparent how the present invention adapter and mating trocar element overcome the shortcomings of the above-mentioned prior art.

Accordingly, the primary objective of the present invention is to provide an economical and practical means for connecting medical tubing to a trocar so as to promote reuse of the trocar upon sterilization.

Other objectives and advantages of the present invention will become apparent to those skilled in the art upon reading the following detailed description and claims, in conjunction with the accompanying drawings which are appended hereto.

BRIEF DESCRIPTION OF THE DRAWINGS

In order to facilitate a fuller understanding of the present invention, reference is now be made to the appended drawings. The drawings should not be construed as limiting the present invention, but are intended to be exemplary only.

PREFERRED EMBODIMENT OF THE PRESENT INVENTION

Figure 1:
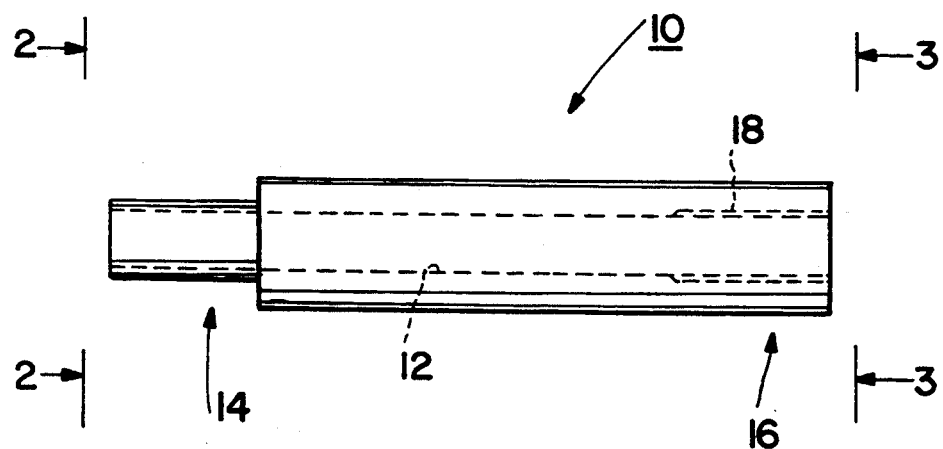
FIG. 1 is a side view of an adapter for use in trocar assemblies according to the present invention.

Referring to FIG. 1, there is shown a side view of an adapter 10 for use in trocar assemblies according to the present invention. The adapter 10, which is preferably fabricated of a rigid material such as hard plastic or metal, is cylindrical in shape with a continuous bore 12 running therethrough. A first end 14 of the adapter 10 has a reduction in outer diameter and a second end 16 of the adapter 10 is internally threaded 18 along the bore 12. The outer diameter of the first end 14 of the adapter 10 is sized so as to allow frictional engagement with the end of a mating flexible tube (see FIG. 7). This frictional engagement is such that the first end 14 of the adapter 10 is friction fit inside the mating flexible tube. To insure that the first end 14 of the adapter 10 is firmly secured to the inside the mating flexible tube, various types of adhesives may be used. The reduction in outer diameter of the first end 14 of the adapter 10 preferably corresponds to the wall thickness of the mating flexible tube so as to maintain a continuous surface of constant outer diameter between the adapter 10 and the mating flexible tube when they are engaged. The second end 16 of the adapter 10 is internally threaded 18 along the bore 12 so as to allow fastenable engagement with a threaded end of a trocar element, which will be described shortly.

Figure 2:
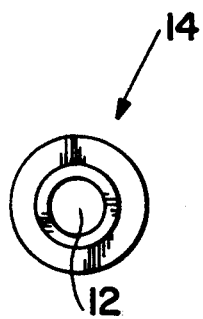
FIG. 2 is an end view of the adapter shown in FIG. 1, taken along line 2—2 of FIG. 1.
Figure 3:
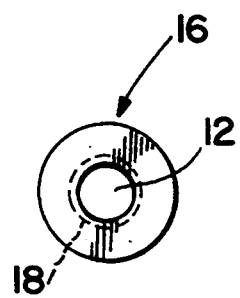
FIG. 3 is an end view of the adapter shown in FIG. 1, taken along line 3—3 of FIG. 1.

Referring to FIG. 2, these is shown an end view of the first end 14 of the adapter 10 shown in FIG. 1, taken along line 2—2 of FIG. 1. Referring to FIG. 3, there is shown an end view of the second end 16 of the adapter 10 shown in FIG. 1, taken along line 3—3 of FIG. 1. It should be noted that since, as previously stated, adhesives are used to firmly secure the first end 14 of the adapter 10 to the inside of the mating flexible tube, and it is not practical to sterilize the mating flexible tube, the adapter 10 and the mating flexible tube should be discarded after one use. Thus, the adapter 10 is preferably fabricated of an inexpensive hard plastic or metal material.

Figure 4:
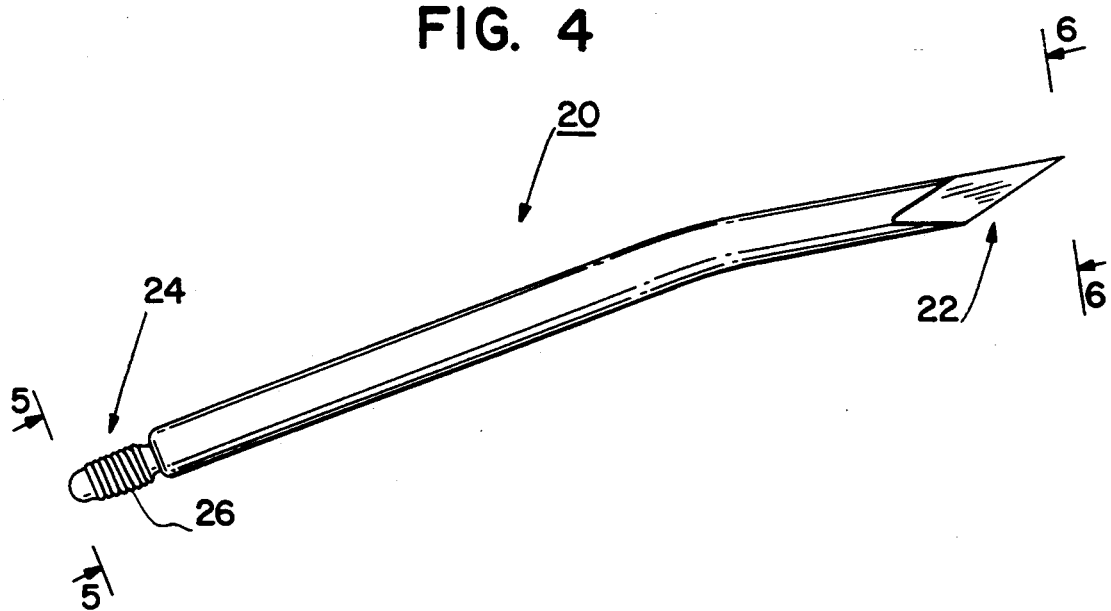
FIG. 4 is a side view of a trocar element for use in trocar assemblies according to the present invention.

Referring to FIG. 4, there is shown a side view of a trocar element 20 for use in trocar assemblies according to the present invention. The trocar element 20 is similar to a traditional trocar element in that it is typically fabricated of metal and has the shape of a rod with a first end 22 being formed with or machined to a sharp point. However, a second end 24 of the trocar element 20 has a reduction in diameter and is threaded 26 so as to mate with the threaded bore 18 of the adapter 10. The reduction in diameter of the second end 24 of the trocar element 20 preferably corresponds to the wall thickness of the threaded bore portion 18 of the adapter 10, so as to maintain a continuous outer surface between the trocar element 20 and the adapter 10 of constant outer diameter when they are mated.

Figure 5:
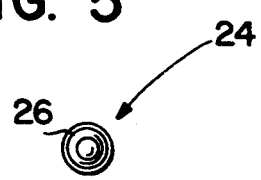
FIG. 5 is an end view of the trocar element shown in FIG. 4, taken along line 5—5 of FIG. 4.
Figure 6:
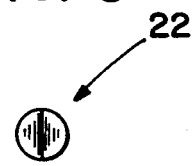
FIG. 6 is an end view of the trocar element shown in FIG. 4, taken along line 6—6 of FIG. 4.

Referring to FIG. 5, there is shown an end view of the second end 24 of the trocar element 20 shown in FIG. 4, taken along line 5—5 of FIG. 4. Referring to FIG. 6, there is shown an end view of the first end 22 of the trocar element 20 shown in FIG. 4, taken along line 6—6 of FIG. 4. It should be noted that the trocar element 20 is typically fabricated of metal since most sterilization procedures are directed towards metal utensils. Thus, the metal trocar element 20 may be reused upon sterilization.

Figure 7:
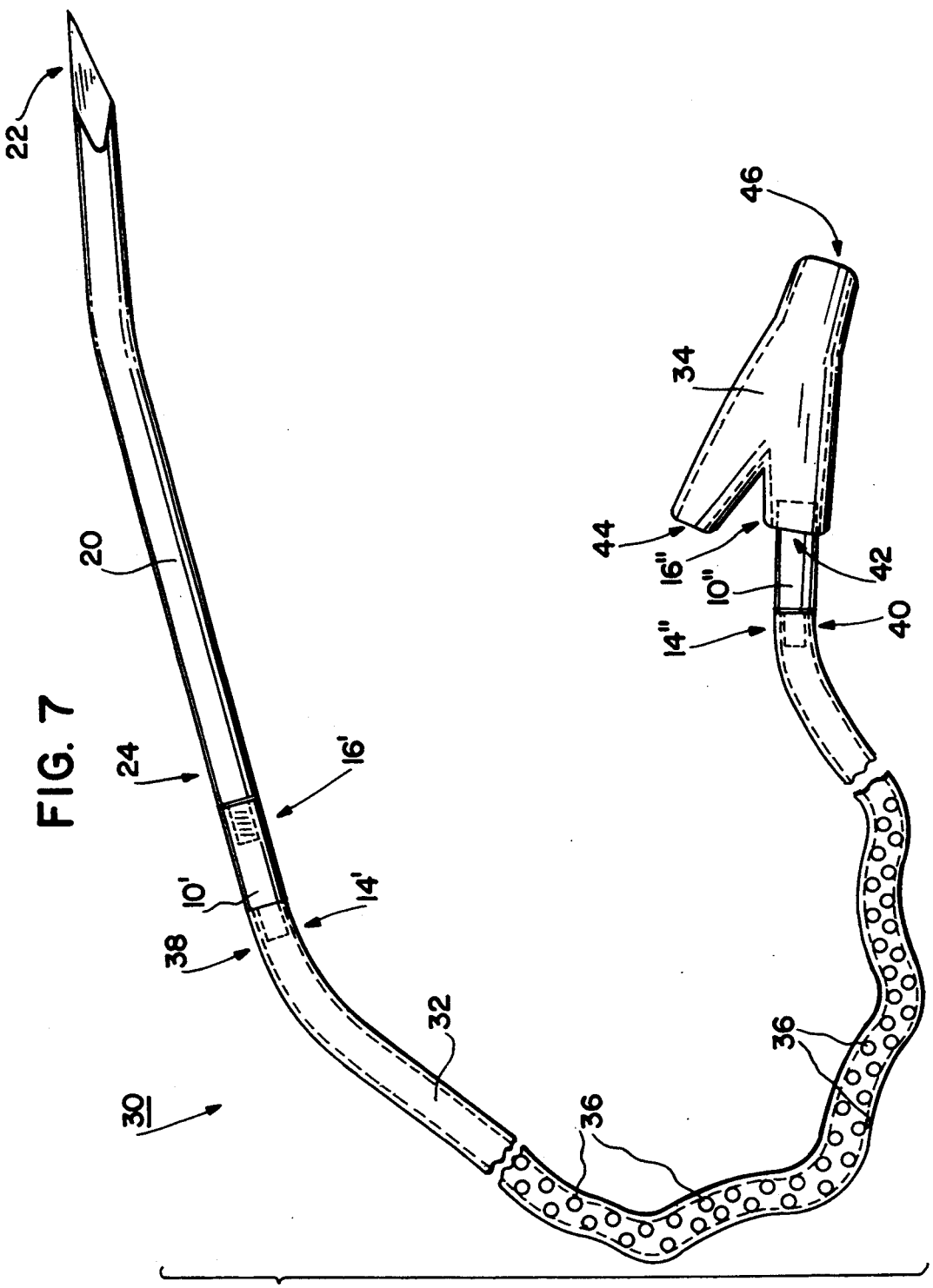
FIG. 7 is an illustration of a trocar assembly using an adapter and a trocar element according to the present invention.

Referring to FIG. 7, there is shown an illustration of a trocar assembly 30 using an adapter 10 and a trocar element 20 according to the present invention. The trocar assembly 30 is comprised of a trocar element 20, a first adapter 10', a flexible tube 32, a second adapter 10'', and a flexible tube junction 34 The flexible tube 32, which is common in trocar assemblies, is fabricated of PVC and has a plurality of regularly spaced pores or perforations 36 formed therein so as to provide for the drainage of fluids. The flexible tube 32 has a first end 38 and a second end 40. The flexible tube junction 34, which is common in the medical field in general, is also fabricated of PVC. The flexible tube junction 34 has a first port 42, a second port 44, and a third port 46 formed therein.

It should be noted that the flexible tube junction 34 is shown to illustrate how either the first adapter 10' or the second adapter 10'' may be frictionally engaged with either the first port 42 or the second port 44 of the flexible tube junction 34, as is commonly the case. Such a flexible tube junction 34 is generally used after a surgical procedure is completed to combine fluids flowing from the first and second ends 38,40 of the flexible tube 32 into a single fluid stream which is then output at the third port 46. Prior to the development of the present invention, the first and second ends 38,40 of the flexible tube 32 would be directly frictionally engaged with the first and second ports 42,44 of the flexible tube junction 34, which could result in the flexible tube 32 collapsing under the frictional engagement pressure of the flexible tube junction 34, or both the flexible tube 32 and the flexible tube junction 34 collapsing under external pressure. Such an occurrence could result in a restriction of fluid flow through the flexible tube 32, a leakage of fluid from between the flexible tube 32 and the flexible tube junction 34, and/or a contamination of fluid by aeration. The rigidness of the adapters 10',10" insures that the adapters 10',10" will not collapse under frictional engagement pressure, or that both the adapters 10',10" and the flexible tube junction 34 will not collapse under substantial external pressure. Furthermore, the rigidness of the adapters 10', 10" provides an easier frictional engagement arrangement.

The threaded end 24 of the trocar element 20 and the threaded bore 16' of the first adapter 10' are fastenably engaged. The reduced diameter end 14' of the first adapter 10' and the first end 38 of the flexible tube 32 are frictionally engaged. Similarly, the second end 40 of the flexible tube 32 and the reduced diameter end 14" of the second adapter 10" are frictionally engaged. However, as previously described, various types of adhesives may be used to insure that the first ends 14',14" of the adapters 10',10" are firmly secured to the ends 38,40 of the mating flexible tube 32, respectively. As just described, the threaded bore end 16" of the second adapter 10" and the first port 42 of the flexible tube junction 34 can be, and herein are shown to be, frictionally engaged. Notice the constant outer diameter continuous surface between the trocar element 20, the first adapter 10', the flexible tube 32, and the second adapter 10". Such a constant outer diameter in the trocar assembly 30 is important since the trocar element 20, the first adapter 10', and the flexible tube 32, must pass through human flesh and body tissues with as little surface resistance as possible. An additional benefit of the adapters 10',10" having the same outer diameter as the flexible tube 32 is that the second ends 16',16" of the adapters 10',10" may be frictionally engaged with any devices that may be frictionally engaged with the flexible tube 32, such as the ports 42,44 of the flexible tube junction 34.

Figure 8:
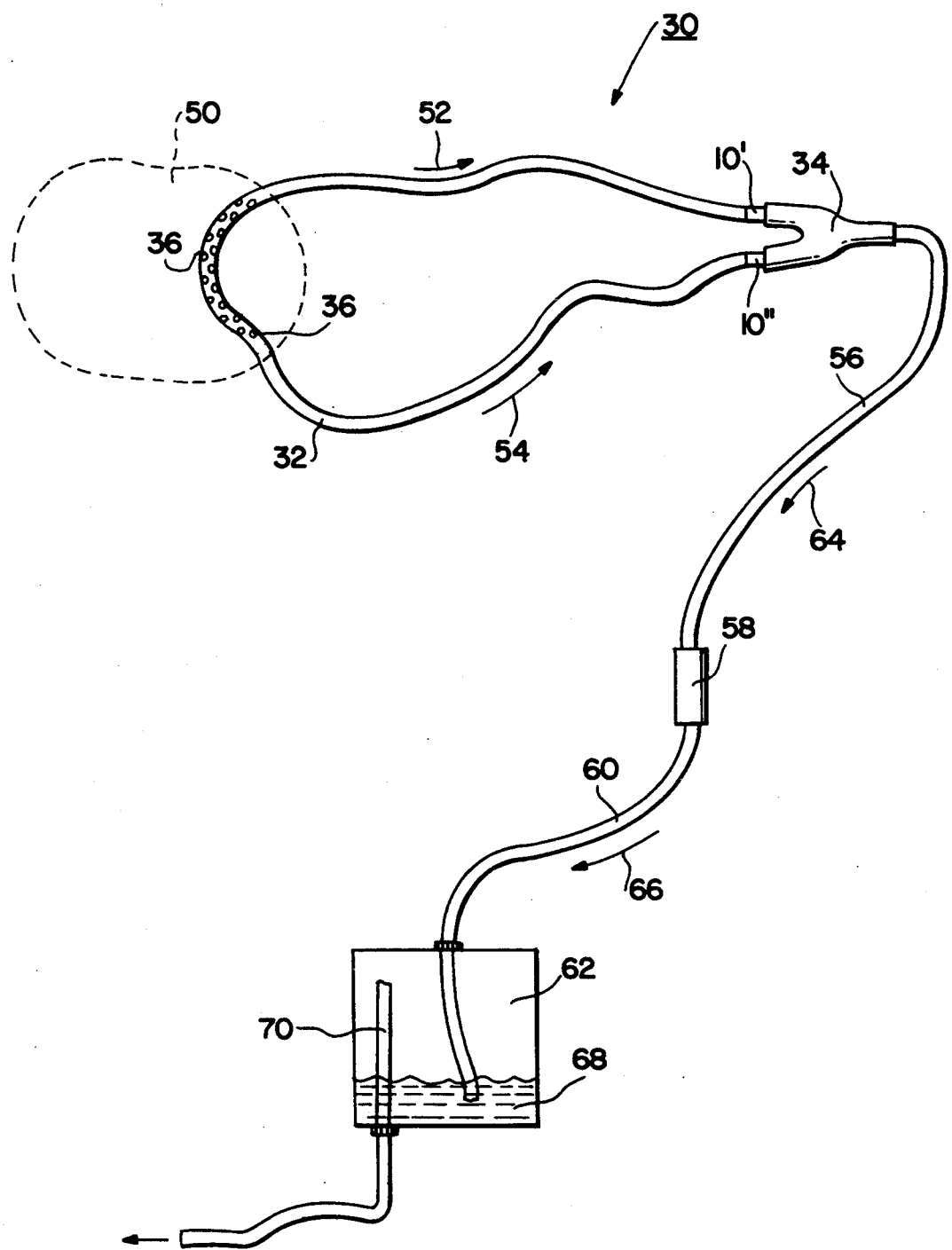
FIG. 8 is an illustration of a typical post-surgical implementation of a trocar assembly with an adapter according to the present invention.

Referring to FIG. 8, there is shown an illustration of the trocar assembly 30 in a typical post-surgical implementation. The flexible tube 32, including the plurality of regularly spaced pores and perforations 36, is imbedded in a patient 50 so as to allow bodily fluids to be drained therefrom. The fluids drain from the patient, as indicated by arrows 52 and 54, through the flexible tube 32 and through the associated adapters 10',10" and are joined at the flexible tube junction 34. The fluids then drain from the flexible tube junction 34, through a second flexible tube 56, a filter 58, and a third flexible tube 60, into a collection chamber 62, as indicated by arrows 64 and 66. The drained fluids 68 collect on the bottom of the collection chamber 62. A tube 70, which is connected to a pump (not shown), is inserted into the collection chamber 62 so as to create a vacuum therein, thereby fostering a forced drainage of the fluids.

Since the trocar assembly 30 is typically used in such a vacuum-based environment, it is an important aspect of the present invention that the adapters 10',10" provide an airtight seal Thus, the adapters 10',10" are not only fabricated so that they will not collapse under frictional engagement pressure, or so that both the adapters 10',10" and the flexible tube junction 34 will not collapse under substantial external pressure, as previously described, but also so that they provide an airtight seal when frictionally engaged with a flexible tube junction 34.

With the present invention adapter 10 and mating trocar element 20 now fully described, it can thus be seen that the primary objective set forth above is efficiently attained and, since certain changes may be made in the above-described adapter 10 and mating trocar element 20 without departing from the scope of the invention, it is intended that all matter contained in the above description or shown in the accompanying drawings shall be interpreted as illustrative and not in a limiting sense.

What is claimed is:

1. An adapter for use in a trocar assembly, said adapter comprising:
   a tubular adapter having an outer cylindrical shape with a continuous bore running therethrough, said adapter having a first end that is reduced in outer diameter, said adapter having a second end, disposed opposite from said first end, that is internally threaded along said bore.

2. The adapter as defined in claim 1, wherein said adapter is fabricated of a rigid material.

3. The adapter as defined in claim 2, wherein said adapter is fabricated of hard plastic.

4. The adapter as defined in claim 2, wherein said adapter is fabricated of metal.

5. A trocar assembly comprising:
   a rod-like trocar element having an outer cylindrical shape, said trocar element having a first end being formed with or machined to a sharp point, said trocar element having a second end, disposed opposite from said first end, that is reduced in outer diameter and is threaded;
   a tubular adapter having an outer cylindrical shape with a continuous bore running therethrough, said adapter having a first end that is reduced in outer diameter, said adapter having a second end, disposed opposite from said first end, that is internally threaded along said bore, said second end of said adapter being internally threaded along said bore so as to allow fastenable engagement with said threaded end of said trocar element.

6. The trocar assembly as defined in claim 5, wherein said second end of said trocar element is reduced in outer diameter by a wall thickness of said threaded end of said adapter so as to maintain a continuous outer surface between said trocar element and said adapter of constant outer diameter when fastenably engaged.

7. The trocar assembly as defined in claim 6, further comprising a flexible tube, said flexible tube having a plurality of regularly spaced pores or perforations formed therein so as to provide for the drainage of fluids situated thereabout, said flexible tube having plurality of ends which may be frictionally engaged with said first end of said adapter.

8. The trocar assembly as defined in claim 7, wherein said first end of said adapter is sized so as to allow frictional engagement with said plurality of ends of said flexible tube, said frictional engagement comprising said first end of said adapter being friction fit inside one of said plurality of ends of said flexible tube.

9. The trocar assembly as defined in claim 7, wherein said frictional engagement further comprises applying an adhesive between said first end of said adapter and said inside of one of said plurality of ends of said flexible tube.

10. The trocar assembly as defined in claim 8, wherein said first end of said adapter is reduced in outer diameter by a wall thickness of said flexible tube so as to maintain a continuous outer surface between said adapter and said flexible mating tube of constant outer diameter when frictionally engaged.

11. The trocar assembly as defined in claim 6, wherein said trocar element is fabricated of metal.

12. The trocar assembly as defined in claim 10, wherein said adapter is fabricated of a rigid material.

13. The trocar assembly as defined in claim 12, wherein said adapter is fabricated of hard plastic.

14. The trocar assembly as defined in claim 12, wherein said adapter is fabricated of metal.

15. The trocar assembly as defined in claim 7, wherein said flexible tube is fabricated of PVC.

16. An adapter for use in a trocar assembly, said adapter comprising:
- a tubular adapter of cylindrical shape having a continuous bore running therethrough, said adapter having a first end and a second end disposed opposite each other, said adapter having a continuous outer diameter except at said first end where said adapter has a reduced outer diameter, said continuous bore being of a continuous inner diameter except at said second end where said continuous bore is internally threaded.

17. The adapter as defined in claim 16, wherein said adapter is fabricated of a rigid material.

18. The adapter as defined in claim 17, wherein said adapter is fabricated of hard plastic.

19. The adapter as defined in claim 17, wherein said adapter is fabricated of metal.

20. A tubular adapter assembly comprising:
- a tubular adapter of cylindrical shape having a continuous bore running therethrough, said adapter having a first end and a second end disposed opposite each other, said adapter having a continuous outer diameter except at said first end where said adapter has a reduced outer diameter, said continuous bore being of a continuous inner diameter except at said second end where said continuous bore is internally threaded; and
- a flexible tube, said flexible tube having an outer diameter equal to said continuous outer diameter of said adapter, said flexible tube having an inner diameter equal to said reduced outer diameter of said adapter, wherein said adapter and said flexible tube are engaged by fitting said first end of said adapter inside an end of said flexible tube, and wherein a continuous outer surface of said continuous outer diameter is maintained between said adapter and said flexible tube during such engagement.

21. The tubular adapter assembly as defined in claim 20, wherein said adapter and said flexible tube are further engaged by applying an adhesive between said first end of said adapter and said end of said flexible tube.

22. The tubular adapter assembly as defined in claim 20, wherein said adapter is fabricated of a rigid material.

23. The tubular adapter assembly as defined in claim 22, wherein said adapter is fabricated of hard plastic.

24. The tubular adapter assembly as defined in claim 22, wherein said adapter is fabricated of metal.

25. The tubular adapter assembly as defined in claim 20, wherein said flexible tube has a plurality of regularly spaced pores or perforations formed therein so as to provide for the drainage of fluids situated thereabout.

26. The tubular adapter assembly as defined in claim 25, wherein said flexible tube is fabricated of PVC.

* * * * *